US011440919B2

(12) United States Patent
Ravishankar et al.

(10) Patent No.: US 11,440,919 B2
(45) Date of Patent: Sep. 13, 2022

(54) C5 SUGAR BASED GELATORS FOR OIL SPILLS

(71) Applicant: HINDUSTAN PETROLEUM CORPORATION LTD., Mumbai (IN)

(72) Inventors: Raman Ravishankar, Bangalore (IN); Chinthalapati Siva Kesava Raju, Bangalore (IN); Bhaskar Pramanik, Bangalore (IN); Peddy Venkat Chalapathi Rao, Bangalore (IN); Venkateswarlu Choudary Nettem, Bangalore (IN); Gandham Sriganesh, Bangalore (IN)

(73) Assignee: Hindustan Petroleum Corporation Ltd., Mumbai (IN)

(*) Notice: Subject to any disclaimer, the term of this patent is extended or adjusted under 35 U.S.C. 154(b) by 255 days.

(21) Appl. No.: 16/312,416

(22) PCT Filed: Dec. 2, 2016

(86) PCT No.: PCT/IN2016/050431
§ 371 (c)(1),
(2) Date: Dec. 21, 2018

(87) PCT Pub. No.: WO2018/002947
PCT Pub. Date: Jan. 4, 2018

(65) Prior Publication Data
US 2019/0241580 A1 Aug. 8, 2019

(30) Foreign Application Priority Data
Jun. 30, 2016 (IN) ............ 201621022612

(51) Int. Cl.
*C07D 493/04* (2006.01)
*B01J 20/28* (2006.01)
*C02F 1/28* (2006.01)
*C02F 1/68* (2006.01)
*C09K 3/32* (2006.01)
*E02B 15/04* (2006.01)
*C02F 101/32* (2006.01)
*C02F 103/00* (2006.01)

(52) U.S. Cl.
CPC ...... *C07D 493/04* (2013.01); *B01J 20/28047* (2013.01); *C02F 1/285* (2013.01); *C02F 1/681* (2013.01); *C09K 3/32* (2013.01); *E02B 15/04* (2013.01); *C02F 2101/32* (2013.01); *C02F 2103/007* (2013.01)

(58) Field of Classification Search
None
See application file for complete search history.

(56) References Cited

U.S. PATENT DOCUMENTS

| | | | | |
|---|---|---|---|---|
| 4,429,140 A | * | 1/1984 | Murai | C07D 493/04 549/370 |
| 5,023,354 A | | 6/1991 | Salome et al. | |
| 5,356,566 A | | 10/1994 | Kobayashi et al. | |
| 6,500,964 B2 | | 12/2002 | Lever et al. | |
| 2015/0025157 A1 | | 1/2015 | Ono et al. | |

FOREIGN PATENT DOCUMENTS

| | | | | |
|---|---|---|---|---|
| EP | 0581024 A1 | | 2/1994 | |
| EP | 2824157 A1 | | 1/2015 | |
| GB | 2113196 A | * | 8/1983 | ......... B01D 17/0214 |
| GB | 2113196 A | | 8/1983 | |

OTHER PUBLICATIONS

Kimura et al. (Theoret. Chim. Acta, 1965, 3, 164-173). (Year: 1965).*
Fuel Oils, 3. Chemical and Physical Information, pp. 105 to 109, accessed online on Jul. 29, 2021 at https://www.atsdr.cdc.gov/toxprofiles/tp75-c3.pdf (Year: 2021).*
International Search Report, dated Mar. 17, 2017 (PCT/IN2016/050431).
Chizhov O S et al: "Mass-spectrometric 1,2 study of carbohydrates a new fragmentation reaction induced by electron impact—"h-rupture, Carbohydrate Research, vol. 6, No. 2, 1968, pp. 138-142, XP028842529, ISSN: 0008-6215, DOI:10.1016/30008-6215(00)81503-7, compounds 3b, 4b.
Tanmoy Kar et al, "Organogelation and Hydrogelation of Low-Molecular-Weight Amphiphilic Dipeptides: pHResponsiveness in Phase-SelectiveGelation and Dye Removal", Langmuir 2009, 25(15), 8639-8648, DOI: 10.1021/la804235e.
Tanmoy Kar et al, "Influence of pristine SWNTs in supramolecular hydrogelation: scaffold for superior peroxidase activity of cytochrome c", Chem. Commun., 2012, 48, 8389-8391, DOI: 10.1039/c2cc33593j.
Vibhute Amol M et al., A Sugar-Based Gelator for Marine Oil-Spill Recovery, Angew. Chem. Int. Ed. 2016, 55, 7782-7785, DOI: 10.1002/anie.201510308.
Vibhute Amol M et al., A Sugar-Based Gelator for Marine Oil-Spill Recovery—Supporting Information.

* cited by examiner

*Primary Examiner* — Clare M Perrin
(74) *Attorney, Agent, or Firm* — Robert L. Stearns; Dickinson Wright, PLLC

(57) ABSTRACT

Sugar-based compounds are provided along with methods for making such compounds. Gels comprising such compounds are also provided along with methods of making gels. Methods of using such compounds for containing spill of a hydrocarbon, and method for reclaiming solvent from gels, comprising such compounds.

10 Claims, No Drawings

C5 SUGAR BASED GELATORS FOR OIL SPILLS

BACKGROUND

1. Technical Field

The subject matter described herein in general relates to sugar-based compounds that are able to form gels. The subject matter further relates to methods of making the sugar-based compounds, and gels including such compounds. The sugar-based compounds can be used to control hydrocarbon spill by gel formation. The subject matter further relates to methods for recovery of hydrocarbons and the sugar based compounds from the gel.

2. Related Art

A gel can be defined as a solution in which the solid, also known as a gelator, is meshed to form a rigid or semi-rigid mixture. Depending on the structural nature of gel networks, gels can be simply divided into chemical gels and physical gels. In the case of chemical gels, the aggregation units at different levels are connected into three-dimensional networks via covalent bonds whereas in physical gels, the molecules of a gelator aggregate into network structure via various non-covalent interactions, which are considerably weaker than covalent bonds.

Physical gelation of water and solvents include polymers, micro- or nano-particles, and low-molecular mass organic compounds (LMMGs). The gels formed by latter are named supramolecular gels or molecular gels and can be used for gelation of oil from oil-water mixtures for oil spill recovery. The spilled oil is transformed from a liquid into semi-solid or rubber-like materials floating on the surface of water by introducing LMMGs into the oil contaminated water.

Kar and co-workers have disclosed supramolecular hydrogelation of a composite including single walled nanotubes (SWNTs) and amphiphilic dipeptide carboxylates (Chem. Commun., 2012, 48, 8389-8391).

Kar and co-workers have disclosed dipeptide-based long-chain acids/salts capable of efficiently gelating organic solvents and water. The xerogels prepared from the organogels showed time-dependent adsorption of dyes such as crystal violet (Langmuir 2009, 25(15), 8639-8648).

SUMMARY

The present disclosure relates to a compound having the Formula:

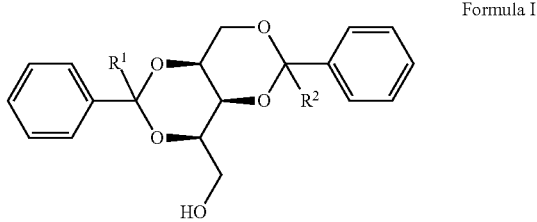

Formula I

Where in, $R^1$ and $R^2$ are independently selected from hydrogen or $C_1$ to $C_6$ alkyl. The present disclosure also relates to a method of preparing the compound of Formula I.

The present disclosure further relates to a gel comprising a compound of Formula I and a solvent. The present disclosure further relates to a method of a gel comprising contacting the compound of Formula I with solvent.

The present disclosure further relates to a method of containing the spill of a hydrocarbon, the method comprising contacting the hydrocarbon with the compound of Formula I to obtain a gel. The present disclosure further relates to a method of reclaiming solvent from the gel comprising a compound of Formula I and a solvent.

These and other features, aspects and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "hydrocarbon(s)" refers to organic compounds that are made of hydrogen and carbon atoms. The source of the hydrocarbons may be from crude oils and refined petroleum products. Crude oil and other petroleum fractions may include compounds with hetero atoms like nitrogen, oxygen, sulfur, halogens and metallic elements along with hydrocarbons.

The term "gel" refers to a colloidal suspension of a solid dispersed in liquid and appears like semi solid.

The term "CRN" means cracked run naptha (mainly comes from the Fluidized Catalytic Cracking (FCC) unit in the refinery).

The term "SRN" means straight run naphtha, which comes from direct distillation of crude oil.

The term "diesel" means a specific fractional distillate of petroleum crude oil between 200° C. and 350° C. at atmospheric pressure.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a temperature range of about 140° C. to about 180° C. should be interpreted to include not only the explicitly recited limits of about 140° C. to about 180° C., but also to include sub-ranges, such as 145° C. to 155° C., 150° C. to 170° C., and so forth, as well as individual amounts, including fractional amounts, within the specified ranges, such as 142.2° C., 140.6° C., and 141.3° C., for example.

The present disclosure relates to a class of amphiphilic gelators which can be used for selective extraction of oil in water systems and water in oil systems. The oil can include, but not limited to, straight run naphtha, gasoline, diesel fractions and crude oil individually and as a mixture of oil and water emulsion. The gelators on contact with the oil absorb the oil and swell to form a gel. This causes phase separation of the oil from the water. The oil absorbed onto the gelators can be easily recovered from the gel by heating the gel. Although the description herewith provided is with reference to the use of gelators in oil spill recovery, it may be understood by a person skilled in the art, that the gelators find use in other areas, such as cosmetics, tissue engineering, drug delivery, separation of biomolecules, and stimulus-responsive advanced materials, as well, albeit with a few variations, as may be understood by a person skilled in the art.

In one implementation, the present disclosure relates to a compound having the Formula:

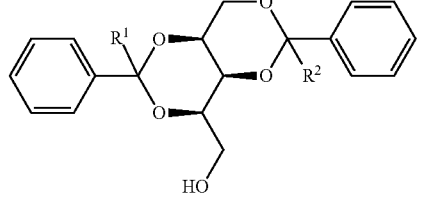

Formula I wherein, $R^1$ and $R^2$ are independently selected from hydrogen or $C_1$ to $C_6$ alkyl.

The present disclosure also relates to a method of preparing the compound of Formula I.

The molecular gelators of Formula I can be used for the containment of spilled refinery products such as straight run naphtha, gasoline, diesel fractions and crude oil individually and as a mixture of oil and water emulsion.

The compounds of Formula I can be used for remediation of a release of spilled crude oil or hydrocarbon.

In one implementation, the present disclosure relates to a compound having the Formula:

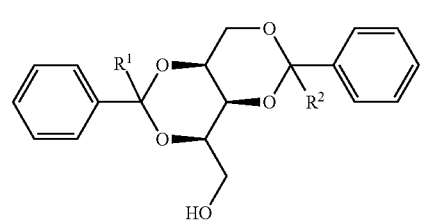

Formula I wherein, $R^1$ is hydrogen and $R^2$ is $C_1$ to $C_6$ alkyl.

In another implementation, the present disclosure relates to a compound having the Formula:

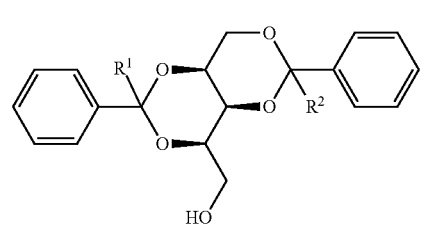

Formula I wherein, $R^1$ is $C_1$ to $C_6$ alkyl and R2 is hydrogen.

In yet another implementation, the present disclosure relates to a compound having the Formula:

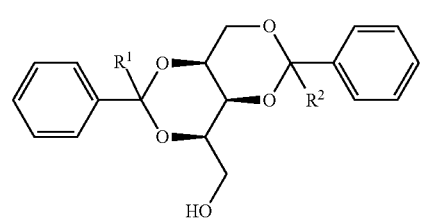

Formula I wherein, $R^1$ and $R^2$ are $C_1$ to $C_6$ alkyl.

In one implementation, the present disclosure relates to a compound having the Formula:

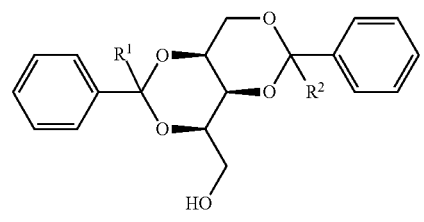

Formula I wherein, $R^1$ and $R^2$ are hydrogen.

In one implementation, the present disclosure relates to a compound having the Formula:

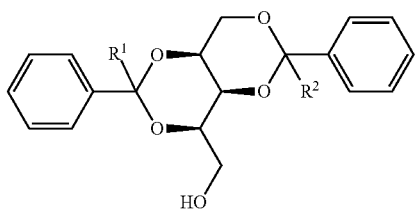

Formula I wherein, R¹ and R² are is $C_1$ alkyl.

In another implementation, the present disclosure relates to a compound having the Formula:

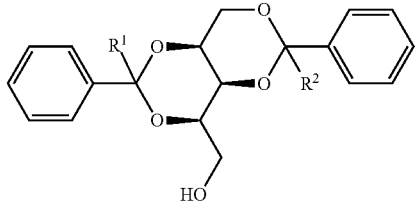

Formula I wherein, R¹ and R² are is $C_2$ alkyl.

In yet another implementation, the present disclosure relates to a compound having the Formula:

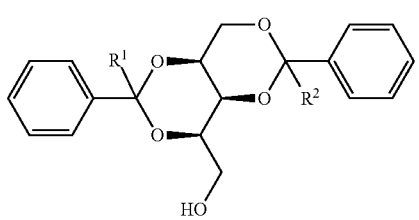

Formula I wherein, R¹ and R² are $C_2$ to $C_4$ alkyl.

In one implementation, the present disclosure relates to a compound having the Formula:

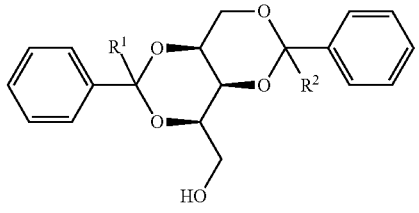

Formula I wherein, R¹ and R² are $C_4$ to $C_6$ alkyl.

In one implementation, the present disclosure relates to a compound having the Formula:

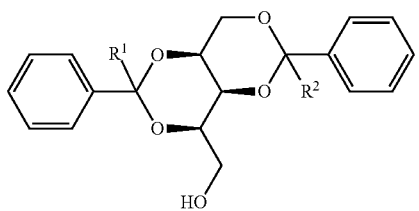

Formula I wherein, R¹ and R² are $C_4$ alkyl.

In another implementation, the present disclosure relates to a compound having the Formula:

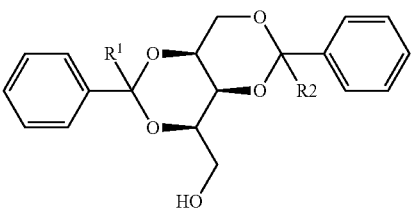

Formula I wherein, R¹ is hydrogen and R² is $C_2$ alkyl.

In one implementation, the present disclosure relates to a compound having the Formula shown below with the substituents as provided in the below Table:

| Compound | IUPAC names | R¹ | R² |
|---|---|---|---|
| 1 | (2,2'-diphenyl-4,4'-bi(1,3-dioxolan)-5-yl)methanol) | H | H |
| 2 | (2,2'-dimethyl-2,2'-diphenyl-4,4'-bi(1,3-dioxolan)-5-yl)methanol) | —$CH_3$ | —$CH_3$ |
| 3 | (2,2'-diethyl-2,2'-diphenyl-4,4'-bi(1,3-dioxolan)-5-yl)methanol) | —$CH_2CH_3$ | —$CH_2CH_3$ |

In one implementation, the present disclosure provides a process for the preparation of compound Formula I, the process comprising the steps of: mixing a non polar solvent and a polar solvent to obtain first solution, contacting xylitol and a reagent to obtain a second solution, adding second solution to the first solution to obtain a solution and reacting the solution with a second reactant to obtain the desired product.

In another implementation, the non polar solvent is selected from the group consisting of cyclohexane, hexane and heptane.

In one implementation, the polar solvent is selected from the group consisting of methanol and ethanol.

In another implementation, the present disclosure provides a process for the preparation of compound Formula I, wherein the step of adding second solution to the first solution to obtain a solution is done at a temperature range of 60-100° C. for 5-20 mins, preferably at a temperature of 70-90° C. for 5-15 mins and most preferably at a temperature of 80° C. for 10 mins.

In another implementation, the reagent is selected from the group consisting of p-TsOH and dodecyl benzene sulfonic acid.

In another implementation, the second reactant is selected from the group consisting of benzaldehyde, acetophenone, and phenyl ethyl ketone.

The process for the preparation of compound Formula I further comprises the purification step.

The compounds of Formula I can be used to form gels. In one implementation, the compounds of Formula I can be added to one or more solvents in order to produce a gel. In another implementation, the compounds of Formula I can be added to a solvent in order to produce a gel.

The present disclosure also relates to a method for producing a gel comprising contacting the compound of Formula I with a solvent. The term solvent refers to a polar solvent, non-polar solvent and mixtures thereof.

In another implementation, the solvent comprises water, an organic solvent, or mixtures thereof. Solvents can be nonpolar such as, for example, hydrocarbons like pentane, cyclopentane, hexane, cyclohexane, benzene, toluene, xylene, 1,4-dioxane, chloroform, diethyl ether or mixtures thereof.

In one implementation, the solvents can be polar, aprotic solvents such as, dichloromethane, tetrahydrofuran, ethyl acetate, acetone, dimethylformamide, acetonitrile, pyridine, carbon disulfide, benzonitrile, or dimethyl sulfoxide.

In another implementation, the solvent can be polar protic solvents such as alcohols and carboxylic acids including, but not limited to, formic acid, n-butanol, isopropanol, n-propanol, ethanol, methanol, acetic acid, ethylene glycol, propylene glycol, glycerin, or water. Mixtures of solvents can also be used herein.

In one implementation, the solvent can be a mixture of water with a hydrocarbon. In another implementation, the solvent is a hydrocarbon. In another implementation, the solvent is selected from crude oil, or a petroleum product.

The gelators of the present disclosure are effective in forming gels in water in oil systems, and oil in water systems. On this account, the gelator is highly versatile, inexpensive, easy to prepare, biodegradable, and non-toxic, unlike the conventionally used gelators.

The present disclosure also relates to method of recovering the spill of a hydrocarbon in a water body. The water body may includes, oceans, seas, rives, etc. In an embodiment, the spill of the hydrocarbon in the water body is recovered by contacting the hydrocarbon with the compound of Formula I to obtain a gel. The formation of gel separates the oil from the water body; the gel is further separated and recovered from the water body to recover the hydrocarbon spill.

In one implementation, a method of recovering crude oil, or petroleum product from a spill of crude oil, or the petroleum product comprises: (a) forming a gel comprising the crude oil, or the petroleum product and a compound of formula I; (b) collecting the gel; and (c) reclaiming the crude oil or the petroleum product from the gel.

In another implementation, method of reclaiming solvent and a compound of Formula I from the gel comprising heating the gel to a suitable temperature for a suitable time to separate the solvent and the compound of Formula I.

EXAMPLES

The disclosure will now be illustrated with working examples, which is intended to illustrate the working of disclosure and not intended to take restrictively to imply any limitations on the scope of the present disclosure. Other examples are also possible which are within the scope of the present disclosure.

Example 1

Synthesis of Compound of Formula I

The compound of Formula I was synthesized according to Scheme 1.

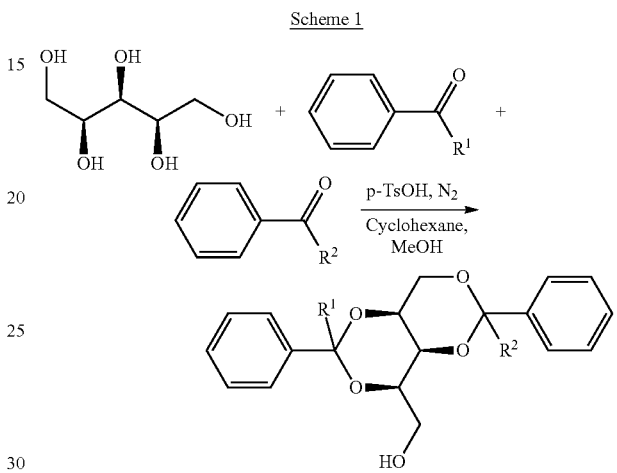

Scheme 1

Sugar based amphiphiles were synthesized by conventional solution phase methodology as represented in Scheme 1. 60 mL cyclohexane was added to a round bottomed flask followed by 15 mL of MeOH and kept under $N_2$ atmosphere. Xylitol (4.2 g, 27.5 mmol) and p-TsOH (0.5 g, 2.7 mmol) was added to the solvent mixture and heated to 80° C. for 10 min. Then benzaldehyde (5.6 ml, 55 mmol) was added to the former solution and the whole mixture was refluxed at 80° C. for 2 hours. After the reaction, solvent was removed under reduced pressure on a rotary evaporator to obtain a white solid. The solid was washed with DCM followed by water and filtered. The product 1 was obtained as a white solid in 90% yield.$^1$H NMR (500 MHz, $CDCl_3$, rt): δ=7.60-7.58 (dd,4H), 7.54-7.52 (t, 2H), 7.41-7.34 (m, 4H), 5.66 (s, 1H), 5.58 (s, 1H), 4.41-4.39 (dd, 1H), 4.16-4.14 (dd, 1H), 4.09-3.97 (m, 3H), 3.86-3.84 (dd, 2H).

Compound 2 was also synthesized following the reaction procedure as that of previous reaction but using acetophenone (27.5 mmol) instead of benzaldehyde. The reaction was performed for 12 hours in this case. The mixture thus obtained after reaction was subjected to washing by DCM and water and the product was isolated as a white solid after drying in 64% yield.$^1$H NMR (500 MHz, $CDCl_3$, rt): δ=7.97-7.95 (d, 4H), 7.58-7.55 (t, 2H), 7.48-7.46 (t, 4H), 4.42-4.39 (dd, 1H), 4.23-4.21 (dd, 1H), 4.08-3.87 (m, 3H), 3.55-3.53 (dd, 2H), 1.68 (s, 6H).

Compound 3 was also synthesized following the reaction procedure as that of compound 1 but using phenyl ethyl ketone (27.5 mmol) instead of benzaldehyde. The reaction was performed for 24 hours in this case. The mixture thus obtained after reaction was subjected to washing by DCM and water where the product was isolated as a white solid after drying in 62% yield.$^1$H NMR (500 MHz, $CDCl_3$, rt): δ=7.97-7.95 (d, 4H), 7.57-7.53 (t, 2H), 7.47-7.43 (t, 4H), 4.43-4.41(dd, 1H), 4.20-4.17 (dd, 1H), 4.05-3.80 (m, 3H), 3.53-3.50 (dd, 2H), 3.03-2.98 (q, 4H), 1.24-1.21 (t, 6H).

Example 2

Gelation Study with Crude Oil

In a typical procedure, 10 mg of the gelator compound of Formula I was added to 0.5 ml of crude oil in a glass vial with an internal diameter (i.d.) of 10 mm The mixture was warmed gently to dissolve the solid compound in crude oil. Then the solution was allowed to cool slowly to room temperature without disturbance. After few minutes, the solid aggregate mass was found to be stable to inversion of the glass vial, and then the compound was recognized to form a gel.

To calculate minimum gelation concentration (MGC), gelator was added gradually from 1 mg to higher amount in required solvent/oil (0.5 ml) and the above process (heating and cooling) was repeated until gel was formed.

Gel melting temperature was determined by typical tube inversion method. The vial containing the gel, as prepared above was immersed in the oil-bath 'upside down' and slowly heated. The temperature at which the viscous gel melted down was recorded as $T_{gel}$.

Gelation Study with Other Oils and Solvents

The gelation process for crude oil was repeated taking CRN, SRN and diesel as refinery distillates and taking hexane, octane, dodecane, hexadecane, benzene, toluene and xylene as solvents (Table 1-3).

TABLE 1

Gelation abilities of compound of Formula I in different hydrocarbon solvents

| | 1 | | 2 | | 3 | |
|---|---|---|---|---|---|---|
| | MGC (% w/v) | MUC (% w/v) | MGC (% w/v) | MUC | MGC (% w/v) | MUC |
| Hexane | P | P | P | ... | P | ... |
| Octane | P | P | P | ... | P | ... |
| Dodecane | 1.8 | 55.5 | 1.91 | 52.3 | P | ... |
| Hexadecane | 1.65 | 60.6 | 1.75 | 57.1 | 1.9 | 52.6 |
| Benzene | 1.16 | 86.2 | 1.22 | 81.9 | 1.43 | 69.9 |
| Toluene | 1.12 | 89.2 | 1.2 | 83.3 | 1.37 | 72.9 |
| Xylene | 1.05 | 95.2 | 1.2 | 83.3 | 1.35 | 74.0 |

MGC = Minimum Gelation Concentration (amount in g of gelator required for 100 ml of hydrophobic material to be gelated),
MUC = Minimum Uptake Capability (volume in ml of hydrophobic material gelated by 1 g of gelator),
P = Precipitate Gelation ability of three compounds is tabulated in the above table. From the table it is quite evident that gelator compounds are more susceptible to form gel with aromatic solvents than paraffinic solvents. Their minimum uptake capability towards aromatic solvents varies in between 70 to 95 times. Gelation ability towards aromatic solvents decreases from 1 to 3 i.e. with increasing carbon number in the molecule hydrophobicity increases making it tough to be soluble. Very poor gelation abilities towards paraffinic solvents are exhibited by these three gelators. All are unable to convert low molecular weight paraffinic solvents e.g. hexane and octane to their respective gel form. However, hexadecane and dodecane can be converted to gel by gelator 1 and 2. Gelator 3 is active only for hexadecane again signifying its poor gelation ability. Thus, higher the molecular weight of the paraffinic solvent lower is the MGC. Superior gelation affinity of these compounds towards aromatic solvents and poor gelation ability for paraffinic solvents might be due to presence of aromatic rings as hydrophobic part in these gelator compounds coming from two capping benzaldehyde/aromatic ketone.

TABLE 2

Gelation abilities of compound of Formula I in different oils

| | 1 | | 2 | | 3 | |
|---|---|---|---|---|---|---|
| | MGC (% w/v) | MUC | MGC (% w/v) | MUC | MGC (% w/v) | MUC |
| CRN | 1.07 | 93.4 | 1.28 | 78.1 | P | ... |
| SRN | 1.31 | 76.3 | P | ... | P | ... |
| Kero | 0.62 | 161.2 | 1.1 | 90.9 | 1.84 | 54.3 |
| Diesel | 0.43 | 232.5 | 0.62 | 161.2 | 0.77 | 129.8 |
| Crude oil | 1.69 | 59.1 | 1.85 | 54.0 | 2.01 | 49.7 |
| Vegetable oil | 0.65 | 153.8 | 0.78 | 128.2 | 0.92 | 108.6 |

MGC = Minimum Gelation Concentration,
MUC = Minimum Uptake Capability,
P = Precipitate All three gelators are capable in transforming crude oil into gel phase with different MGC values. Along with crude oil, different refinery distillates also converted to gel by the gelator compounds as depicted in Table 2. Poor gelation ability of these compounds with paraffinic solvents is reflected in their gelation abilities with refinery distillates also. As SRN have least aromatic content than other distillates, the gelation efficiency for SRN was found to be lowest; even gelator 2 and 3 was unable to form gel with SRN. CRN having higher percentage of unsaturations e.g. olefins and aromatics is converted to gel easily than SRN. As we move from lighter fractions to heavier fractions (from SRN to Diesel via Kero) aromatic content gradually increases resulting successive increment of gelation ability by these gelators. Thus heavier refinery distillates are easily gelated than the lighter distillates. Crude oil having complex composition have poor gelation tendency than its various fractions where minimum uptake capability for crude oil was found to be in between 49 to 59 times whereas, maximum gelation ability is observed for diesel (up to 232 times). Comparison of gelation ability of 1-3 for crude oil as well for other oils dictates superior gelation ability of 1 followed by 2 and 3. Gelation ability of three gelators for vegetable oil was also proved, exhibiting minimum uptake capabilities ranging from 108 to 153 times.

TABLE 3

Gelation abilities of compound of Formula I in different crude oils

| | 1 | | 2 | | 3 | |
|---|---|---|---|---|---|---|
| | MGC (% w/v) | MUC | MGC (% w/v) | MUC | MGC (% w/v) | MUC |
| (C1, API = 18.8) | 2.33 | 42.9 | 2.42 | 41.3 | 2.53 | 39.5 |
| (C2, API = 27.1) | 2.1 | 47.6 | 2.2 | 45.4 | 2.35 | 42.5 |
| (C3, API = 28.1) | 2.106 | 47.4 | 2.12 | 47.1 | 2.22 | 45.0 |
| (C4, API = 35.5) | 1.69 | 59.1 | 1.85 | 54.0 | 2.01 | 49.7 |
| (C5, API = 40.5) | 1.92 | 52.0 | 2.1 | 47.6 | 2.21 | 45.2 |

MGC = Minimum Gelation Concentration,
MUC = Minimum Uptake Capability

In order to check the effect of the composition of crude oil on the gelation ability of the organogelator, experiments were conducted with crudes with varying API gravities ranging from very low API (C1, 18.8°) to high API (C5, 40.5°). Table 3 describes the effect of API gravity (crude composition) on the uptake (MGC) capability of the gelators. Higher gelation ability is again exhibited by 1 than 2 and 3. It is evident from Table 3 that heavy crude (lower API) have higher MGC and lighter crude (higher API) have lower MGC and the uptake capability decreased with increase in API gravity. Higher the resins & asphaltenes content in the crude, lower is its API gravity. Thereby a reduction in the uptake capacity with lowering API may be attributed to successive percentage increase of resins & asphaltenes content in crude oil. This trend is discontinued when moving from API 35.5 to 40.5 and this phenomenon can be explained according to higher paraffinic content in extra light crude (API 40.5) as these gelators have poor gelation capability for paraffinic solvents. However, minimum uptake capability ranging from 40 to 60 times for various crude oils are quite remarkable regarding compositional complexities of the crude oils. These findings indicate that the composition of crude oil played a major role in the oil uptake capability by the gelator compounds. Hence these gelators could be used for the most of the crudes covering the wide spectrum of crude basket available from different parts of the globe.

Example 3

Selective Gelation of crude oil from a Biphasic Mixture of Oil and Water

In a typical procedure, 0.5 mL of crude oil and 0.5 mL of water were taken in a sample tube to which 10 mg of the gelator compound of Formula I (as required to attain at least MGC) was added (Table 4). The gelator was then solubilized in this two-phase solution by heating. After the mixture was cooled to room temperature, the crude oil layer was gelated, keeping the water layer intact in the liquid state. The same process was followed for other oils like CRN, SRN, Kero, diesel and vegetable oil.

TABLE 4

Gelation abilities of compound of Formula I in various oil-water mixtures

|  | 1 | | 2 | | 3 | |
| --- | --- | --- | --- | --- | --- | --- |
|  | MGC (% w/v) | MUC | MGC (% w/v) | MUC | MGC (% w/v) | MUC |
| CRN-Water | 1.2 | 83.3 | 1.31 | 76.3 | P | ... |
| SRN-Water | 1.4 | 71.4 | P | ... | P | ... |
| Kero-Water | 0.65 | 153.8 | 1.17 | 85.4 | 1.85 | 54.0 |
| Diesel-Water | 0.5 | 200 | 0.73 | 136.9 | 0.8 | 125 |
| Crude-water | 1.8 | 55.5 | 1.96 | 51.0 | 2.05 | 48.7 |
| Veg Oil-Water | 0.7 | 142.8 | 0.81 | 123.4 | 0.98 | 102.0 |

MGC = Minimum Gelation Concentration,
MUC = Minimum Uptake Capability

Selective gelation of oil from a biphasic mixture of oil and water was performed and the results are noted in Table 4. Six oil samples containing crude oil, refinery distillates as well as vegetable oil were subjected for gelation experiment prior to practical application in oil spillage. All three gelators were able to gelate exclusively the oil phase without altering the water phase during performance evaluation gelation experiments. Gelation abilities of the gelators follow the same order as reported in Table 2 i.e. gelation ability of 1>2>3. SRN was unable to be gelated by 2 and 3 whereas CRN was unable to be gelated by 3. Selective gelation of other oils was successful and there was no significant alteration in their gelation abilities in biphasic mixture as compared to that of individual oils from table 2. MGCs for all oils were increased not more than 0.2% (w/v) from their respective individual/single phase studies. Thus, oil over water can be contained using these gelators leaving water phase unaffected.

Example 4

Selective Gelation of Crude Oil from a Biphasic Mixture of Oil and Salt Solution:

In a typical procedure, 0.5 mL of crude oil and 0.5 mL of 3.5% of NaCl solution (equivalent salt concentration to that of sea water) were taken in a sample tube to which required of the gelator compound of Formula I was added. The gelator was then solubilized in this two-phase solution by heating. After the mixture was cooled to room temperature, the crude oil layer was gelated, keeping the water layer intact in the liquid state. The same process was followed for other oils like CRN, SRN, Kero, diesel and vegetable oil.

TABLE 5

Gelation abilities of compound of formula I in various oil-sea water mixture

|  | 1 | | 2 | | 3 | |
| --- | --- | --- | --- | --- | --- | --- |
|  | MGC (% w/v) | MUC | MGC (% w/v) | MUC | MGC (% w/v) | MUC |
| CRN-Sea Water | 1.2 | 83.3 | 1.35 | 74.07 | P | ... |
| SRN-Sea Water | 1.38 | 72.4 | P | ... | P | ... |
| Kero-Sea Water | 0.65 | 153.8 | 1.2 | 83.3 | 1.85 | 54.0 |
| Diesel-Sea Water | 0.48 | 208.3 | 0.75 | 133.3 | 0.82 | 121.9 |
| Crude-Sea water | 1.81 | 55.2 | 1.95 | 51.2 | 2.1 | 47.6 |
| Veg Oil-Sea Water | 0.7 | 142.8 | 0.8 | 125 | 1.0 | 100 |

MGC = Minimum Gelation Concentration,
MUC = Minimum Uptake Capability

Oil Selective gelation of oils from a biphasic mixture of oil and sea water was also performed and the results are tabulated in Table 5. Again the gelator compounds 1-3were able to gelate exclusively the oil phase without altering the sea water phase during performance evaluation gelation experiments. Comparison of the results from Table 4 and Table 5 clearly dictates that even under highly saline conditions MCG & MUC for those oils remained almost unchanged. Thus, strength and capability of the organogelators towards gelation for organic phase is highly encouraging even under extreme conditions reveling practical application towards oil spillage recovery over sea.

Example 5

Oil Spill Recovery:

Oil spill recovery was performed taking 10 ml of SRN over 20 ml of water. An ethanolic solution of the compound of Formula I (0.25 g in 5 mL of ethanol, 5 w/v %; only 2.5 ml of the ethanolic solution was used for 10 ml of SRN) was added to the SRN-water mixture and allowed to stand for about 15 min where SRN phase was transformed to the gel keeping the water layer intact in the liquid state. The gel phase was filtered off and processed to recover the oil.

Example 6

Room Temperature Gelation of Crude Oil from a Biphasic Mixture of Oil and Salt Solution:

For the phase selective gelation purpose volatile and oil miscible solvent dichloromethane (DCM) was used. In a typical procedure 10% solution of the gelator was prepared by dissolving it in DCM at room temperature without applying heat. To a 25 ml of crude oil layer over 100 ml of salt solution the gelator solution was applied to ensure complete dispersion. Within a few minutes volatile DCM is evaporated and the crude oil layer is transformed to the gel state. Utilizing the volatile solvent e.g. DCM, phase selective gelation of crude oil as well as other oil fraction are possible. The advantage of this process is that without applying any heating and cooling process phase selective gelation is possible making the process very much economical. Thus the process can be applied for larger scale for practical remediation of oil spillage. Generally use of other hydrophobic solvent e.g. toluene, diesel or SRN for phase selective gelation require excess amount of gelator to congeal the oil phase as well as carrier solvent but, applying our above said process these drawbacks can be neglected and maximum efficiency can be achieved.

Example 7

Reclaiming Solvent from Gel 10 ml of SRN was transformed into gel phase using 80 mg of compound of Formula I. The gel was then subjected to vacuum distillation for oil phase recovery. After successful distillation 8.9 ml of SRN was recovered leaving white powder of the gelator compound with 89% of solvent recovery. The vacuum distillation was carried out at 60° C. for 1 hour.

Advantages Gained in the Example Illustrative Process in this Subject Matter:

Environmentally benign sugar based phase selective gelator has been developed for oil phase gelation from a mixture of oil and water. The gelators efficiently work even at a very low concentration and at room temperature. The gelators find application in marine oil spill recovery. Oil from the gel can be recovered and gel can be recycled and reused for number of cycles without loss of activity Although the subject matter has been described in considerable detail with reference to certain examples and implementations thereof, other implementations are possible. As such, the spirit and scope of the appended claims should not be limited to the description of the preferred examples and implementations contained therein.

We claim:

1. A formulation for containing a spill of a hydrocarbon, the formulation consisting of a compound of Formula I and a polar solvent, wherein the compound of Formula I is:

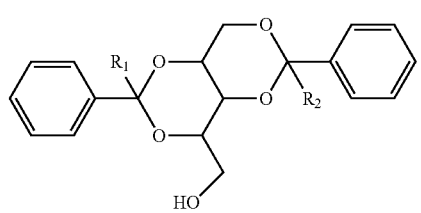

Formula I wherein, $R_1$ is selected from $C_1$ to $C_6$ alkyl; and $R_2$ is selected from $C_1$ to $C_6$ alkyl.

2. The formulation as claimed in claim 1, wherein $R_1$ and $R_2$ are independently selected from $C_1$ to $C_2$ alkyl.

3. The formulation as claimed in claim 1, wherein the polar solvent is any of: a polar protic solvent and a polar aprotic solvent.

4. The formulation as claimed in claim 1, wherein the polar solvent is a polar protic solvent selected from the group consisting of formic acid, n-butanol, isopropanol, n-propanol, ethanol, methanol, acetic acid, ethylene glycol, propylene glycol and glycerin.

5. The formulation as claimed in claim 1, wherein the polar solvent is a polar aprotic solvent selected from the group consisting of dichloromethane, tetrahydrofuran, ethyl acetate, acetone, dimethylformamide, acetonitrile, pyridine, benzonitrile and dimethyl sulfoxide.

6. A gel consisting of a compound of Formula I and a solvent, wherein the compound of Formula I is:

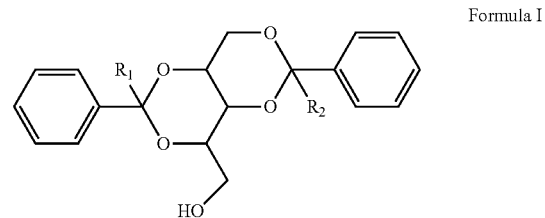

Formula I wherein, $R_1$ is selected from $C_1$ to $C_6$ alkyl; and $R_2$ is selected from $C_1$ to $C_6$ alkyl, and
wherein the solvent is a hydrocarbon or a mixture of hydrocarbon and water.

7. A method for containing a spill of a hydrocarbon, the method comprising contacting the hydrocarbon with a formulation consisting of a compound of Formula I and a polar solvent, wherein the compound of Formula I is:

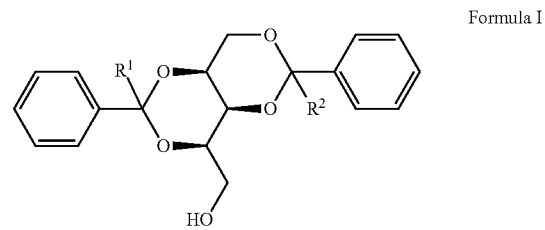

Formula I wherein, $R_1$ is selected from $C_1$ to $C_6$ alkyl; and $R_2$ is selected from $C_1$ to $C_6$ alkyl.

8. The method as claimed in claim 7, wherein the polar solvent is selected from any of: a polar protic solvent and a polar aprotic solvent.

9. The method as claimed in claim 7, wherein the polar solvent is a polar protic solvent selected from the group consisting of formic acid, n-butanol, isopropanol, n-propanol, ethanol, methanol, acetic acid, ethylene glycol, propylene glycol and glycerin.

10. The method as claimed in claim 7, wherein the polar solvent is a polar aprotic solvent selected from the group consisting of dichloromethane, tetrahydrofuran, ethyl acetate, acetone, dimethylformamide, acetonitrile, pyridine, benzonitrile and dimethyl sulfoxide.

* * * * *